United States Patent [19]

Kluy et al.

[11] 4,003,921

[45] Jan. 18, 1977

[54] PROCESS FOR THE PRODUCTION OF AZOMETHINES

[75] Inventors: Werner Kluy, Stiepel; Hans Feichtinger; Jurgen Falbe, both of Dinslaken, all of Germany

[73] Assignee: Ruhrchemie Aktiengesellschaft, Germany

[22] Filed: May 1, 1975

[21] Appl. No.: 573,729

Related U.S. Application Data

[63] Continuation of Ser. No. 326,181, Jan. 24, 1973, abandoned.

[30] Foreign Application Priority Data

Jan. 24, 1973 Germany .......................... 2205791

[52] U.S. Cl. .......................... 260/347.7; 260/566 R
[51] Int. Cl.$^2$ .................................... C07C 119/00

[58] Field of Search ..................... 260/566 R, 347.7

[56] References Cited

UNITED STATES PATENTS 2,422,013   6/1947   Haury et al. .................. 260/566 R

*Primary Examiner*—Gerald A. Schwartz
*Attorney, Agent, or Firm*—Bierman & Bierman

[57] ABSTRACT

An azomethine is produced by reacting a saturated or unsaturated aliphatic, cycloaliphatic, aromatic or heterocyclic aldehyde with ammonia and hydrogen in the presence of a catalyst containing at least one group VIII B metal at a temperature of 20° to 200° C. Preferably, the catalyst also contains at least one group VI B metal.

14 Claims, No Drawings

PROCESS FOR THE PRODUCTION OF AZOMETHINES

This is a Continuation application of Ser. No. 326,181, filed Jan. 24, 1973, now abandoned, and which claims the priority of German P 22 05 791,6-42, filed Feb. 8, 1972.

The process of producing azomethines (Schiff's bases) from primary amines and aldehydes by dehydration is known and has numerous applications. It can be performed with aldehydes and amines, which may be of the aliphatic, cycloaliphatic, aromatic or heterocyclic type (Houben-Weyl, Vol VII/1, page 454, Vol. XI/2, page 73 ff and British patent 1 173 982). Azomethine compounds can also be prepared by reacion of aldimines or ketimines with primary amines; ammonia or amine being, respectively, split off. Reactive carbonyl compounds are frequently condensed, preferably in the form of their corresponding acetals, with amines to Schiff's bases (Houben-Weyl, Vol. XI/2, page 78). Azomethine compounds represent valuable intermediate products for further syntheses (Houben-Weyl, Vol XI/2, page 85). For instance, alkylidenealkylamines can readily be converted to secondary amines by treatment with hydrogen under pressure (Houben-Weyl, Vol XI/1, page 618 ff).

It is an object of the present invention to provide a method of producing an azomethine from any saturated or unsaturated aldehyde, ammonia and hydrogen at atmospheric pressure and in one step.

This is accomplished by reacting a saturated or unsaturated aliphatic, cycloaliphatic, aromatic or heterocyclic aldehyde with ammonia and hydrogen at a temperature of 20° to 200° C in the presence of a catalyst containing at least one metal of group VIII B of the periodic table of elements.

It is highly surprising, that with the novel process of the present invention further conversion of azomethines to secondary amines can be suppressed by maintaining determined reaction conditions, so that the desired reaction products are obtained in high yields. It is also of great importance, that the azomethines are generally obtained in high purity. Thus, purification operations, which, due to the thermal instability of some azomethine compounds, might result in a significant decrease of the yield, can be omitted.

With the process of the present invention, staturated and unsaturated aliphatic, cycloaliphatic, aromatic or heterocyclic aldehydes prepared by any process, as for example, by the oxosynthesis, can be converted to azomethines. It is truly surprising and remarkable, that unsaturated aldehydes are not hydrogenated under the conditions of the process of the instant invention.

The starting materials may be converted in stoichiometric amounts, viz. aldehyde, ammonia and hydrogen are converted in a molar ratio of 2:1:1. It is however most advantageous, to use excess ammonia and hydrogen, based upon the amount of aldehyde, with a volume ratio of ammonia to hydrogen of 1:1. Deviations of the hereinbefore mentioned molar ratio will not adversely effect the course of the reaction, providing care is taken, that at least stoichiometric amounts of the individual reactants are present.

The aldehydes to be converted by the process according to the present invention can be employed in the reaction in solution form or as is viz. undissolved. Suitable inert solvents for the aldehydes include for example aliphatic, cycloaliphatic or aromatic hydrocarbons as well as alcohols. Advantageously, the amount of solvent employed should not exceed the weight of the aldehyde to be converted.

Although the reaction can be performed even at ambient temperature, the use of elevated temperatures is preferred, since it decreases the reaction time. Temperatures in the range of 80° to 140° C are especially preferred.

According to the present invention, catalysts containing at least one metal of group VIII B of the periodic table can be used. The applicability of the catalysts of the present invention is independant of the manner of their preparation. For example, carrier-catalysts prepared respectively by precipitation or by impregnation as well as carrier-free catalysts, for instance of the Raney-metal type, are suitable. Preferably, the catalysts also contain at least one metal of group VI B of the periodic table of elements. Chromium is especially preferred.

Catalysts containing at least one metal selected from the group consisting of iron, cobalt and nickel, preferable nickel, together with at least one compound of a metal of group VI B of the periodic table, preferably Chromium (3)-oxide, are advantageous.

Especially well suited are nickel containing carrier-catalysts, to which activators, such as, for instance, magnesium oxide or aluminium oxide, have been added. Examples of preferred catalyst compositions are as follows:

1. nickel (56–57% by weight, based on the weight of the catalyst composition), magnesium oxide and carrier material.
2. nickel (about 25% by wieght, based on the weight of the catalyst composition), aluminium oxide and carrier material.
3. nickel (about 50% by wieght, based on the weight of the catalyst composition), chromium (3)-oxide and carrier material.
4. nickel (about 52–53% by weight, based on the weight of the catalyst composition, chromium (3)-oxide and carrier material.

The catalysts are preferably used in the pulverulent state and, according to their activity, in amounts between about 5 to about 10% by weight, based upon the amount of the aldehyde. They are advantageously used in reduced activated form. It is however also possible to use reduced and stabilized catalysts, since these are converted to the active form during the reaction.

Water formed during the reaction is substantially removed from the reaction mixture by the gas stream. It may however also be removed from the reaction system in any other way known in the art, as for example by azeotropic distillation.

After a reaction time of one to several hours the reaction product is freed from the catalyst by filtration or centrifuging. Since the reaction generally proceeds quantitatively, very pure azomethines are frequently obtained. These may be used directly, without further purification, for subsequent conversions. If desired, a purification stage, for instance vacuum distillation, may be provided after the preparation step; however the thermal instability of some azomethines should first be considered.

The reaction according to the present invention may be conducted in a discontinuous or continuous manner. When the reaction is performed discontinuously, aldehyde, catalyst and if desired a solvent, are charged into a stirring vessel equipped with cooling means. Ammonia and hydrogen are introduced into the resulting suspension. The amount of gas introduced per hour into the reaction system depends upon the conversion velocity. Generally the higher the temperature the greater the amount of gas introduced into the reaction.

The following examples are offered only for the purpose of illustrating the method of the present invention and are not intended to limit same. In the examples, the presence and composition of the produced azomethines was ascertained by IR-spectra.

EXAMPLE 1

1000g isobutyraldehyde and about 100 g of a commercially available nickel containing carrier catalyst (containing about 52 to 53% by weight nickel, and employing chromium (3)-oxide as activator) are introduced into a 2 l three-necked flask, equipped with a gas inlet tube, a stirrer and a reflux condensor, and cooled to −15° C. Hydrogen and ammonia are introduced into the resulting suspension in a volume ratio of 1 : 1 and at a temperature of 90° C. 160 l of gas are introduced per hour. Altogether, 240 l hydrogen and 240 l gaseous ammonia are introduced. After termination of the reaction, the catalyst is separated by filtration. 889 g isobutylidene — isobutylamine are obtained.

| Analysis: (% by weight) | N | C | H |
|---|---|---|---|
| Calculated: | 11.1 | 75.6 | 13.4 |
| Determined: | 10.7 | 75.4 | 13.2 |

EXAMPLE 2

1000 g n-butyraldehyde are reacted in the presence of 80 g of a commercially available nickel containing carrier catalyst (containing about 52 to 53% by weight nickel, and employing chromium (3)-oxide as activator) at 115° C with ammonia and hydrogen (volume ratio 1 : 1) in a flask equipped as described in Example 1. Altogether 260 l ammonia and 260 l hydrogen are introduced into the aldehyde-catalyst-suspension over a period of 4 hours. After termination of the reaction, the catalyst is separated from the reaction mixture. 840 g butylidene-butylamine are obtained.

| Analysis: (% by weight) | N | C | H |
|---|---|---|---|
| Calculated: | 11.1 | 75.6 | 13.4 |
| Determined: | 10.2 | 75.8 | 13.1 |

EXAMPLE 3

1000 g 3-methylbutanal are reacted in the presence of 100 g of a commercially available nickel containing carrier catalyst (containing about 52 to 53% by weight nickel and employing chromium (3)-oxide as activator) at 110° C with a mixture of ammonia and hydrogen (volume ratio 1:1) in a flask equipped as described in Example 1. The velocity of the gases is 160 l/h. Altogether, 240 l ammonia and 240 l hydrogen are introduced into the catalyst suspension over a reaction time of 3 hours. After termination of the reaction the catalyst is separated by filtration. 868 g 3-methylbutylidene-3-methylbutylamine are obtained.

| Analysis: (% by weight) | N | C | H |
|---|---|---|---|
| Calculated: | 9.0 | 77.4 | 13.5 |
| Determined: | 8.1 | 77.7 | 13.6 |

EXAMPLE 4

1000 g 2-ethylhexenal are reacted in the presence of 80 g of a commercially available nickel containing carrier catalyst (containing about 52 to 53% by weight nickel, and employing chromium(3)-oxide as activator) at 98° C with ammonia and hydrogen (volume ratio 1 : 1) in a flask equipped as described in Example 1. The velocity of the respective gases is 85 l/h. Altogether, 340 l gaseous ammonia and 340 l hydrogen are introduced into the catalyst suspension during a reaction time of 4 hours, corresponding to a gas velocity of 170 l/h. After separation of the catalyst, 916 g of an unsaturated azomethine of 2-ethylhexenal are obtained.

| Analysis: (% by weight) | N | C | H |
|---|---|---|---|
| Calculated: | 5.8 | 80.2 | 13.8 |
| Determined: | 5.4 | 80.1 | 13.7 |

EXAMPLE 5

1000 g isononylaldehyde are reacted in the presence of 100 g of a commercially available nickel containing carrier catalyst (containing about 52 to 53% by weight nickel, and employing chromium (3)-oxide as activator) at 110° C with ammonia and hydrogen (volume ratio 1 : 1) in a flask equipped as described in Example 1. The gas velocity amounted to 180 l/h. Altogether, 180 l hydrogen are used. After termination of the reaction, the catalyst is separated by filtration. 926 g isononylidene-isononylamine are obtained.

| Analysis: (% by weight) | N | C | H |
|---|---|---|---|
| Calculated: | 5.2 | 80.9 | 13.9 |
| Determined: | 5.4 | 80.5 | 13.6 |

EXAMPLE 6

1000 g benzaldehyde are reacted in the presence of 80 g of a commercially available nickel containing carrier catalyst (containing about 52 to 53% by weight nickel, and employing chromium (3)-oxide as activator), at a temperature of 120° C, with ammonia and hydrogen in a flask equipped as described in Example 1. Altogether, 540 l ammonia-hydrogen-mixture (volume ratio 1 : 1), corresponding to gas velocity of 180 l/h, are introduced into the catalyst suspension during a reaction time of 3 hours. After separation of the catalyst, 908 g benzylidene-benzylamine are obtained.

| Analysis: (% by weight) | N | C | H |
|---|---|---|---|
| Calculated: | 7.2 | 86.2 | 6.7 |
| Determined: | 7.0 | 86.5 | 6.6 |

EXAMPLE 7

1000 g furfural are reacted in the presence of 120 g of a commercially available nickel containing carrier catalyst (containing about 52 to 53% by weight nickel, and employing chromium (3)-oxide as activator), at 140° C with ammonia and hydrogen, in a flask equipped as described in Example 1. 640 l of a mixture of ammonia and hydrogen (volume ratio 1 : 1) are introduced into the catalyst suspension, at a gas velocity of 160 l/h during a reaction time 4 hours. After separation of the catalyst, 867 g furfurylidene-furfurylamine are obtained.

| Analysis: (% by weight) | N | C | H | O |
|---|---|---|---|---|
| Calculated: | 8.0 | 68.6 | 5.2 | 18.3 |
| Determined: | 8.2 | 68.3 | 5.0 | 17.9 |

EXAMPLE 8

In a flask as described in Example 1, 1000 g 2-phenylpropanal are reacted in the presence of 90 g of a commercially available nickel containing carrier catalyst (containing about 52 to 53% by weight nickel, and employing chromium (3)-oxide as activator) at a temperature of 130°, with a total of 300 l ammonia and hydrogen (volume ratio 1 : 1) during a reaction time of 2 hours. After termination of the reaction, the catalyst is separated by filtration. 921 g 2-phenylpropylidene-2-phenylpropylamine are obtained.

| Analysis: (% by weight) | N | C | H |
|---|---|---|---|
| Calculated: | 5.6 | 84.4 | 8.0 |
| Determined: | 5.6 | 84.6 | 8.1 |

The high purity of the azomethines obtained according to the invention is of special advantage if they are used as intermediate products for further syntheses known in the art (Houben/Weyl, Vol. XI/2, page 78). If they are used as starting materials, high yields of pure final products are attained. This is true even if they are hydrogenated to secondary amines. Furthermore azomethines are valuable anticaking agents for the preparation of granulated fertilizers.

What is claimed is:
1. A process for the production of an azomethine, which comprises reacting a saturated or unsaturated aliphatic, cycloaliphatic, aromatic or heterocyclic aldehyde with ammonia and hydrogen at atomspheric pressure and at a temperature of 20° to 200° C in the presence of a catalyst containing at least one metal of group VIII B of the periodic table.
2. The process according to claim 1, wherein said catalyst additionally contains a group VI B metal.
3. The process according to claim 2, wherein said group VI B metal is chromium.
4. The process according to claim 1, wherein said group VIII B metal is iron, cobalt or nickel.
5. The process according to claim 2, wherein said group VIII B metal is iron, cobalt or nickel.
6. The process according to claim 3, wherein said group VIII B metal is iron, cobalt or nickel.
7. The process according to claim 4, wherein said group VIII B metal is nickel.
8. The process according to claim 5, wherein said group VIII B metal is nickel.
9. The process according to claim 6, wherein said group VIII B metal is nickel.
10. The process according to claim 1, wherein said temperature is 80° to 140° C.
11. The process according to claim 1, wherein the aldehyde ammonia and hydrogen are reacted in at least stoichiometric amounts.
12. The process according to claim 1, wherein the aldehyde, ammonia and hydrogen are respectively present in a molar ratio of 2 : 1 : 1.
13. The process according to claim 1, wherein the ammonia and hydrogen are respectively present in a molar ratio of 1 : 1 and are respectively employed in an amount in excess of the stoichiometric amount required for reaction with the aldehyde.
14. The process according to claim 1, wherein said catalyst is employed in an amount about 5% to about 10% by weight, based upon the amount of the aldehyde.

* * * * *